United States Patent [19]

Abel et al.

[11] Patent Number: 4,605,798
[45] Date of Patent: Aug. 12, 1986

[54] CONTINUOUS PROCESS FOR THE GASEOUS-PHASE PREPARATION OF TRICHLOROTRIFLUOROETHANE, DICHLOROTETRAFLUOROETHANE AND MONOCHLOROPENTAFLUOROETHANE IN CONTROLLED PROPORTIONS

[75] Inventors: Michel Abel, Pierre-Benite; Francois Fine, St. Laurent de Mure; Louis Foulletier, Oullins; Yvan Verot, Ecully, all of France

[73] Assignee: PCUK Products Chimiques Ugine Kuhlmann, Courbevoie, France

[21] Appl. No.: 324,823

[22] Filed: Nov. 25, 1981

[30] Foreign Application Priority Data

Dec. 31, 1980 [FR] France .................. 80 27865

[51] Int. Cl.[4] .......................... C07C 17/00
[52] U.S. Cl. ..................... 570/164; 570/163; 570/165; 570/166; 570/167; 570/168; 570/169
[58] Field of Search ............ 570/163, 164, 165, 166, 570/167, 168, 169

[56] References Cited

U.S. PATENT DOCUMENTS

| | | | |
|---|---|---|---|
| 2,478,362 | 8/1949 | Benning | 570/167 |
| 3,157,707 | 11/1964 | Clark et al. | 570/169 |
| 3,455,840 | 7/1969 | Kato et al. | 570/168 |
| 3,632,834 | 1/1972 | Christoph | 570/168 |
| 3,793,229 | 2/1974 | Groppelli et al. | 570/163 |

FOREIGN PATENT DOCUMENTS

| | | | |
|---|---|---|---|
| 731700 | 4/1966 | Canada | 570/167 |
| 117964 | 2/1976 | Fed. Rep. of Germany | |
| 119033 | 4/1976 | Fed. Rep. of Germany | |
| 1544361 | 4/1968 | France | |
| 26729 | 8/1973 | Japan | 570/167 |
| 896068 | 5/1962 | United Kingdom | 570/168 |

OTHER PUBLICATIONS

L. Marangoni, et al., "Preparation of Chloropentafluoroethane from Dichoro Tetrafluoro Ethane," J. Fluor, Chem., 19, pp. 21-34 (1981/82).

Primary Examiner—Charles F. Warren
Assistant Examiner—Joseph A. Boska
Attorney, Agent, or Firm—Pennie & Edmonds

[57] ABSTRACT

This invention relates to a continuous gaseous-phase process for the preparation of trichlorotrifluoroethane, dichlorotetrafluoroethane and monochloropentafluoroethane, in predetermined proportions, from tetrachloroethylene, chlorine and hydrofluoric acid in the presence of a catalyst. The process is characterized by the combination of two chlorination-fluorination reactors in sequence, a parallel fluorination-dismutation reactor, and a separation unit for extracting the desired products and recycling recovered hydrofluoric acid and non-fluorinated or insufficiently fluorinated products. The process advantageously yields dichlorotetrafluoroethane containing less than 7% asymmetric isomer, and trichlorotrifluoroethane containing less than 2% asymmetric isomer.

9 Claims, 1 Drawing Figure

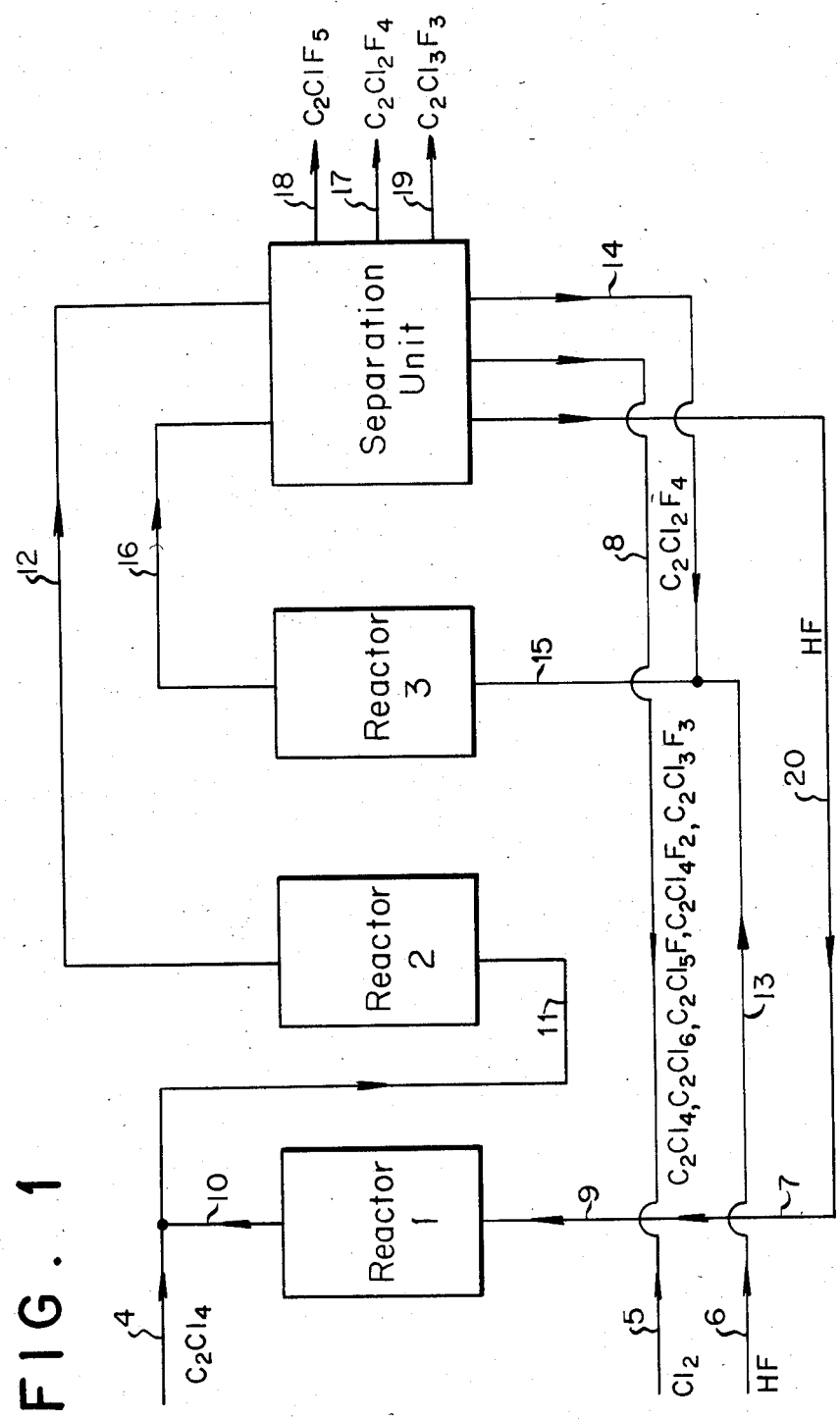

CONTINUOUS PROCESS FOR THE GASEOUS-PHASE PREPARATION OF TRICHLOROTRIFLUOROETHANE, DICHLOROTETRAFLUOROETHANE AND MONOCHLOROPENTAFLUOROETHANE IN CONTROLLED PROPORTIONS

TECHNICAL FIELD

This invention relates to a continuous gaseous-phase process for the preparation of trichloro-1,1,2-trifluoro-1,2,2-ethane, dichloro-1,2-tetrafluoro-1,1,2,2-ethane and chloro-1-pentafluoro-1,1,2,2,2-ethane, yielding these three compounds in predetermined proportions from tetrachloroethylene, chlorine and hydrofluoric acid.

BACKGROUND ART

The catalytic fluorination reactions of hexachloroethane, formed in situ by the addition of chlorine to tetrachloroethylene have long been known.

A currently used process consists of performing these reactions in a liquid phase, in the presence of an antimony halide catalyst. This process easily yields trichloro-1,1,2-trifluoro-1,2,2-ethane, but obtaining dichloro-1,2-tetrafluoro-1,1,2,2-ethane requires high reaction temperatures which involves considerable corrosion of the equipment. Obtaining chloro-1-pentafluoro-1,1,2,2,2-ethane in significant quantities is practically impossible. Moreover, the activity of the catalysts, used in the liquid phase, is very sensitive to the impurities of the reagents, involving extended purifications and raising the cost of the process. Small quantities of pentahaloethanes, which are difficult to separate, are also formed.

Other processes also achieve these gaseous-phase fluorination reactions on various catalysts, such as the oxides or halides of chromium, aluminum, cobalt, iron, titanium, nickel, copper, palladium or zirconium, at temperatures on the order of 200° to 450° C.

These gaseous-phase processes also have a number of disadvantages. The primary disadvantage is the formation, more important in the gaseous phase than in the liquid phase, of trichloro-1,1,1-trifluoro-2,2,2-ethane and dichloro-1,1-tetrafluoro-1,2,2,2-ethane. These isomers, called asymmetric, of trichloro-1,1,2-trifluoro-1,2,2-ethane and dichloro-1,2-tetrafluoro-1,1,2,2-ethane, are undesirable since they are more reactive, and consequently more unstable, than the so-called symmetric isomers. It is acknowledged that for many commercial applications trichlorotrifluoroethane should contain less than 2% of the trichloro-1,1,1-trifluoro-2,2,2-ethane isomer; also, the dichlorotetrafluoroethane should contain less than 15%, and preferably less than 7% of the dichloro-1,1-tetrafluoro-1,2,2,2-ethane asymmetric isomer.

Another disadvantage of the standard gaseous-phase processes is the difficulty of controlling the reaction temperature, because of the strong exothermicity of the reaction of addition of chlorine on tetrachloroethylene.

A third disadvantage results from the deactivation of the catalyst, caused by the polymerization of tetrachloroethylene on the catalytic surface.

Finally, it is difficult to obtain a predetermined distribution of trichlorotrifluoroethane, dichlorotetrafluoroethane and monochloropentafluoroethane with the known gaseous-phase fluorination processes.

To partially relieve these disadvantages, various solutions have been recommended. Thus, U.S. Pat. No. 3,632,834 teaches that the use of a specific catalyst with a chromium trifluoride base in the gaseous phase yields trichlorotrifluoroethane containing not more than about 2% of the trichloro-1,1,1-trifluoro-2,2,2-ethane isomer and dichlorotetrafluoroethane containing not more than about 15% of the dichloro-1,1-tetrafluoro-1,2,2,2 ethane isomer. But this process does not yield chloropentafluoroethane and the transformation rate of hydrofluoric acid does not exceed 62%.

U.S. Pat. No. 3,157,707 describes a process of preparing tetrachlorodifluoroethane, trichlorotrifluoroethane, dichlorotetrafluoroethane and chloropentafluoroethane by passage, in a gaseous phase, of a mixture of tetrachloroethylene, chlorine and hydrofluoric acid over a catalyst having a $Cr_2O_3$ base. The asymmetric isomers are produced in small, imprecise quantities. A particular embodiment of this process consists of, first, having the chlorine and tetrachloroethylene react on a $Cr_2O_3$—based catalyst at a temperature of 200° to 350° C., then mixing the effluents with the hydrofluoric acid before sending them into a second zone of chromium oxide catalysis, reaching a temperature of 300° C. This variation only yields trichlorotrifluoroethane and dichlorotetrafluoroethane.

In order to obtain trichlorotrifluoroethane, dichlorotetrafluoroethane and chloropentafluoroethane in controlled proportions, Japanese Patent Application No. 73.26729 recommends a combination of liquid phase and gaseous phase reactions. In a first stage, tetrachloroethylene, chlorine and hydrofluoric acid are made to react in the liquid phase under pressure over a catalyst having an antimony trichloride base, and the raw trichlorotrifluoroethane formed is isolated. The latter is then sent in the gaseous phase in the presence of hydrofluoric acid over an aluminum trifluoride-based catalyst. At 320° C. under 5 atmospheres, 60% of the trichlorotrifluoroethane is converted into dichlorotetrafluoroethane. If the reaction is conducted at 440° C. under 5 atmospheres, a practically quantitative yield of chloropentafluoroethane is obtained. The principal disadvantage of this process is a poor utilization of the heat in the reaction between chlorine and tetrachloroethylene and the relatively large quantities of asymmetric isomers of trichlorotrifluoroethane and dichlorotetrafluoroethane obtained during the gaseous-phase fluorination.

U.S. Pat. No. 118,221 of the German Democratic Republic describes the gaseous-phase preparation of chloropentafluoroethane from a mixture of tetrachloroethylene, chlorine andd hydrofluoric acid. This mixture is first sent to a first catalysis zone which is heated at 350° C. and contains an aluminum trifluoride catalyst doped with nickel fluoride; then, the effluents pass into a second catalysis zone, containing a chromium oxide catalyst heated at 350° C. Trichlorotrifluoroethane, dichlorotetrafluoroethane and hexafluoroethane are formed as by-products. The major disadvantages of this process are the use of two different catalysts, no easy control over the proportions of the products formed, and very high amounts of $C_2Cl_3F_3$ and $C_2Cl_2F_4$ asymmetric isomers.

The applicants' French Pat. No. 1,453,510 teaches a process for purification of dichlorotetrafluoroethane to enrich the symmetric isomer, which consists of having the isomer mixture, possibly in the presence of hydrofluoric acid and/or chlorine, pass, in a gaseous or liquid state, at temperatures between 50° and 500° C., over a catalyst chosen from active carbon, activated alumina, molecular sieves, aluminum fluoride, salts of chromium, cobalt, aluminum, copper, iron or molybdenum, whether or not deposited on a support such as active carbon or alumina. When it is applied in the presence of hydrofluoric acid, this process causes two distinct reactions—a fluorination reaction of dichlorotetrafluoroethane, yielding chloropentafluoroethane, $C_2Cl_2F_4 + HF \rightarrow C_2ClF_5 + HCl$, with accessory formation of very small amounts of hexafluoroethane; and a dismutation reaction of dichlorotetrafluoroethane, yielding chloropentafluoroethane and trichlorotrifluoroethane, $2C_2Cl_2F_4 \rightarrow C_2ClF_5 + C_2Cl_3F_3$. Since the dichlorotetrafluoroethane asymmetric isomer in these two reactions is more reactive than the symmetric isomer, the result is an enrichment of the untransformed dichlorotetrafluoroethane into a symmetric isomer.

DISCLOSURE OF THE INVENTION

The applicants have now discovered that in the gaseous-phase preparation of trichlorotrifluoroethane and dichlorotetrafluoroethane from chlorine, hydrofluoric acid and tetrachloroethylene:
- the conversion rate of hydrofluoric acid becomes weaker as the number of fluorine atoms to be fixed becomes higher;
- the weaker the conversion rate of hydrofluoric acid, the smaller the amount of asymmetric isomer reaction products; and
- an excess of chlorine maintains the activity of the fluorination catalysts longer.

The applicants have also discovered that in the preparation of chloropentafluoroethane and the enrichment of dichlorotetrafluoroethane into an asymmetric isomer according to the process in French Pat. No. 1,453,510, the presence of trichlorotrifluoroethane and/or hydrochloric acid in the reagents lowers, in an appreciable manner, the enrichment rate of dichlorotetrafluoroethane into a symmetric isomer. Moreover, the presence of hydrochloric acid has an inhibiting role on the fluorination reaction of dichlorotetrafluoroethane into monochloropentafluoroethane.

These observations have led the applicants to conceive a continuous catalytic process for the gaseous-phase preparation of trichlorotrifluoroethane with small amounts of asymmetric isomer, dichlorotetrafluoroethane, also with a low content of asymmetric isomer, and monochloropentafluoroethane, in controlled proportions, from chlorine, hydrofluoric acid and tetrachloroethylene, characterized by the combination of the following steps and means:

(a) a first chlorination-fluorination reaction zone, fed by chlorine, hydrofluoric acid and recycled products: $C_2Cl_4$, $C_2Cl_6$, $C_2Cl_5F$, $C_2Cl_4F_2$ and $C_2Cl_3F_3$, working with an excess of chlorine in relation to $C_2Cl_4$ and a small conversion rate of hydrofluoric acid;

(b) a second chlorination-fluorination reaction zone mounted in sequence with the first, fed with fresh tetrachloroethylene and operating preferably at a temperature lower than reaction zone 1;

(c) a third, fluorination-dismutation reaction zone, mounted parallel with the first two, fed with hydrofluoric acid and dichlorotetrafluoroethane that has been recycled from a separation unit;

(d) the separation unit, in which, by standard means, the reaction gases are treated in such a way as to recover the untransformed hydrofluoric acid and extract the desired quantities of chloropentafluoroethane, dichlorotetrafluoroethane and trichlorotrifluoroethane, enriched with symmetric isomers, while the untransformed tetrachloroethylene and hexachloroethane, pentachlorofluoroethane, tetrachlorodifluoroethane and the excess of trichlorotrifluoroethane are sent to feed the first reaction zone and the excess of dichlorotetrafluoroethane is recycled to feed the third reaction zone.

BRIEF DESCRIPTION OF THE DRAWINGS

For a better understanding of the process of this invention, the operation is shown schematically in FIG. 1.

MODES FOR CARRYING OUT THE INVENTION

Reactor 1 is fed by 9 with a mixture of chlorine, from storage 5, fresh and recovered hydrofluoric acid, arriving in 7 and coming from storage 6 and from recycling 19, and recycled products, coming from 8 of the separation unit and made up of tetrachloroethylene, hexachloroethane, pentachlorofluoroethane, tetrachlorodifluoroethane and trichlorotrifluoroethane. The introduced chlorine is excessive in relation to the recycled tetrachloroethylene. The gases leaving from 10 of reactor 1 are mixed with fresh tetrachloroethylene, coming from storage 4, in such a way that the total molar ratio of chlorine introduced in 9 to fresh tetrachloroethylene is between about 0.95 and 1.05.

The mixture is sent by pipe 11 to the entrance of reactor 2 which is at a lower temperature than reactor 1. The effluents of reactor 2 pass by pipeline 12 to the separation unit. They are essentially made up of dichlorotetrafluoroethane, trichlorotrifluoroethane tetrachlorodifluoroethane, pentachlorofluoroethane, hexachloroethane, tetrachloroethylene, hydrofluoric acid and hydrochloric acid.

Reactor 3 is fed by 15 with a mixture of hydrofluoric acid, delivered by pipeline 13, and dichlorotetrafluoroethane, recycled from the separation unit and delivered by pipeline 14. The effluents of reactor 3 are sent to the separation unit by pipe 16.

At the exit of the separation unit, the desired quantity of dichlorotetrafluoroethane is collected in 17; the rest is recycled to reactor 3 by pipeline 14. The extracted dichlorotetrafluoroethane contains less than 7% asymmetric isomer. Chloropentafluoroethane is extracted in 18. Through pipe 19, the desired quantity of trichlorotrifluoroethane is extracted, containing less than 2% asymmetric isomer; the rest is mixed with tetrachloroethylene, hexachloroethane, pentachlorofluoroethane and tetrachlorodifluoroethane leaving in line 8 from the separation unit. The untransformed hydrofluoric acid is recycled through pipe 20.

The catalysts used in reactors 1 and 2 can be standard and known fluorination catalysts, such as oxides or halides of chromium, aluminum, cobalt, iron, titanium, nickel, copper, palladium or zirconium used as they are or on supports. However, it is especially advantageous to use catalysts having a microsphere base of chromium oxide, described in French Patent Application No. 80.27659; catalysts with an active carbon base impregnated with chromium sulfate, described in French Patent Application No. 80.27660; catalysts with an active carbon base impregnated with chromium trioxide, described in French Patent Application No. 80.27661; and catalysts with a base of chromium salts or oxides and aluminum phosphate, described in French Patent Application No. 80.27662. These catalysts by themselves yield a high rate of symmetric isomers of trichlorotrifluoroethane and dichlorotetrafluoroethane. The above French patent applications are in the name of the assignee of this application.

The catalysts used in reactor 3 for the fluorination-dismutation reaction of dichlorotetrafluoroethane can be the catalysts described in French Pat. No. 1,453,510, but the catalysts cited in the aforementioned French Patent Applications, Nos. 80.27659, 80.27660, 80.27661 and 80.27662, are also suitable.

In order to facilitate the exploitation of the process, it is preferable to use the same catalyst in the three reactors, but this is not mandatory.

The fluorination and fluorination-dismutation catalysts can be used in a fixed bed, but it is preferable to use them in a fluidized bed, which contributes to increasing their life. In fact, these catalysts are tainted by the formation of tar on their surface. The use of a fluidized bed causes the elimination of this tar by the simple abrasion of the grains rubbing against each other. The fluidization also very precisely controls the functioning temperature of the catalyst, insures good homogeneity of this temperature, and reduces the undesirable formation of perfluorinated derivatives and also pentahalogenated derivatives resulting from cracking of the molecules. In addition, the utilization of fluidized bed reactor aids in keeping the activity of the catalyst constant by partial regular renewal of the latter, without interrupting the functioning of the equipment.

The process of the invention can function at pressures from about 0.1 to 20 bars. The choice of pressure for the functioning is fixed by technological and economic considerations.

The temperature of the reaction can go from about 250° to 500° C.; the temperature of reactor 1 always advantageously being higher than that of reactor 2. These temperatures are regulated according to the desired distribution of the products in the reaction.

The time of contact of the gases with the catalyst can vary from 1 to 20 seconds, also depending on the desired distribution of the products in the reaction.

The molar rato of chlorine to tetrachloroethylene is in the aggregate very close to 1 (between 0.95 to 1.05) but at the entrance to the first reactor the excess chlorine is between about 1.1 and 5.0.

According to an advantageous embodiment of the process of the invention, the reaction temperature of the first reaction zone is between about 300° and 500° C., the temperature of the second reaction zone is between about 250° and 450° C. and the temperature of the third reaction zone is between about 250° and 500° C.

For the first two reactors, the molar ratio of hydrofluoric acid to tetrachloroethylene depends on the desired distribution of trichlorotrifluoroethane and dichlorotetrafluoroethane.

For the third reactor, the molar ratio of hydrofluoric acid to dichlorotetrafluoroethane can vary from between about 0.1 to 1, according to the quantity of chloropentafluoroethane desired.

EXAMPLES

The following are provided as examples illustrating various aspects of the process of the invention, but not limited to them. All the parts mentioned are in moles. In all the examples, the extracted dichlorotetrafluoroethane contains less than 7% asymmetric isomer and the extracted trichlorotrifluoroethane contains less than 2% asymmetric isomer.

EXAMPLE 1

The three reactors in the operation are fluidized bed reactors, supplied with the same chromium oxide catalyst in the form of microspheres, as described in French Patent Application No. 80.27659.

The desired distribution of the products in the reaction is:

| | |
|---|---|
| trichlorotrifluoroethane | 14% moles |
| dichlorotetrafluoroethane | 70% moles |
| chloropentafluoroethane | 16% moles |

To do this, the following operating conditions are chosen:

| | |
|---|---|
| Reactor 1: | |
| Temperature | 330° C. |
| Pressure | 2.0 absolute atmospheres |
| Contact time | 2.6 seconds |
| Feed to Reactor 1: | |
| $Cl_2$ | 100 parts |
| HF | 425 parts |
| Recycled $C_2Cl_4$ | 65 parts |
| Recycled $C_2Cl_6$, $C_2Cl_5F$ and $C_2Cl_4F_2$ | 35 parts |
| Recycled $C_2Cl_3F_3$ | 35 parts |

At the exit, the transformation rate of hydrofluoric acid is 75%.

| | |
|---|---|
| Reactor 2: | |
| Temperature | 290° C. |
| Pressure | 1.5 absolute atmosphere |
| Contact time | 2.2 seconds |

FEED TO REACTOR 2

Effluents from the first reactor with 100 parts fresh $C_2Cl_4$ added.

At the exit, the total transformation rate of hydrofluoric acid is above 91.7%.

The organic part of the effluents contains:

| | |
|---|---|
| Untransformed $C_2Cl_4$ | 65 parts |
| $C_2Cl_6$, $C_2Cl_5F$ and $C_2Cl_4F_2$ | 35 parts |
| $C_2Cl_3F_3$ | 45 parts |
| $C_2Cl_2F_4$ | 90 parts |

After separation of the constituents in the separation unit, the dichlorotetrafluoroethane is sent to reactor 3 at the same time as 28 parts of hydrofluoric acid.

Reactor 3 is maintained at 330° C. under a pressure of 0.3 absolute atmosphere and the contact time is 5.6 seconds.

The following products are obtained:

| | |
|---|---|
| $C_2Cl_3F_3$ | 4 parts |
| $C_2Cl_2F_4$ | 70 parts |
| $C_2Cl\ F_5$ | 16 parts |

All the dichlorotetrafluoroethane and chloropentafluoroethane are extracted from the operation at the same time as 16 parts of trichlorotrifluoroethane. The rest of the trichlorotrifluoroethane is recycled to the entrance of reactor 1 with the other less-fluorinated products.

EXAMPLE 2

The same catalyst is used as in Example 1, but a different distribution of products of the reaction is desired, that is:

| $C_2Cl_3F_3$ | 23% moles |
| $C_2Cl_2F_4$ | 68% moles |
| $C_2ClF_5$ | 9% moles |

The operating conditions of the reactors are as follows:

| Reactor 1 | |
| --- | --- |
| Temperature | 405° C. |
| Pressure | 1.9 absolute atmosphere |
| Contact time | 4.6 seconds |
| Feed to Reactor 1: | |
| $Cl_2$ | 100 parts |
| HF | 415 parts |
| Recycled $C_2Cl_4$ | 28 parts |
| Recycled $C_2Cl_6$, $C_2Cl_5F$ and $C_2Cl_4F_2$ | 72 parts |
| Recycled $C_2Cl_3F_3$ | 35 parts |

At the exit, the transformation rate of hydrofluoric acis is 56.6%.

| Reactor 2: | |
| --- | --- |
| Temperature | 285° C. |
| Pressure | 1.4 absolute atmosphere |
| Contact time | 4.6 seconds |

FEEDING TO REACTOR 2

Effluents from reactor 1 with 100 parts fresh $C_2Cl_4$ added. At the exit of reactor 2, the total transformation rate of hydrofluoric acid reaches 91.3%.

The organic part of the effluents has the following composition:

| Untransformed $C_2Cl_4$ | 28 parts |
| $C_2Cl_6$, $C_2Cl_5F$ and $C_2Cl_4F_2$ | 72 parts |
| $C_2Cl_3F_3$ | 55 parts |
| $C_2Cl_2F_4$ | 80 parts |

After separation of the products of the reaction, the dichlorotetrafluoroethane is sent to reactor 3 at the same time as 44 parts of hydrofluoric acid. Reactor 3 functions at 395° C. under 0.7 atmosphere with a contact time of 4.9 seconds. The following are formed:

| $C_2Cl_3F_3$ | 3 parts |
| $C_2Cl_2F_4$ | 68 parts |
| $C_2ClF_5$ | 9 parts |

All of the chloropentafluoroethane, all of the dichlorotetrafluoroethane and 23 parts of the trichlorotrifluoroethane are extracted from the operation. The rest of $C_2Cl_3F_3$ is recycled to the first reactor with the other less-fluorinated products.

EXAMPLE 3

The three fluidized bed reactors are provided with the same chromium oxide catalyst deposited on active carbon, as described in French Patent Application No. 80.27661.

To obtain the following distribution of the products in the reaction:

| $C_2Cl_3F_3$ | 78.9% |
| $C_2Cl_2F_4$ | 17.3% |
| $C_2ClF_5$ | 3.8% | the following operating conditions are chosen:

| Reactor 1: | |
| --- | --- |
| Temperature | 375° C. |
| Pressure | 2.1 absolute atmospheres |
| Contact time | 7.3 seconds |

The feed to reactor 1 comprising the following mixture:

| $Cl_2$ | 100 parts |
| HF | 341 parts |
| Recycled $C_2Cl_4$ | 50 parts |
| Recycled $C_2Cl_6$, $C_2Cl_5F$ and $C_2Cl_4F_2$ | 50 parts |
| Recycled $C_2Cl_3F_3$ | 29 parts |

The transformation rate of hydrofluoric acid in the reactor is 66%.

| Reactor 2: | |
| --- | --- |
| Temperature | 300° C. |
| Pressure | 1.2 absolute atmosphere |
| Contact time | 7.3 seconds |

The feed reactor 2 comprises the effluents from reactor 1 with 100 parts of fresh $C_2Cl_4$ added.

At the exit, the total transformation rate of hydrofluoric acid rises to 95%.

The organic part of the effluents is made up of:

| Untransformed $C_2Cl_4$ | 50.0 parts |
| $C_2Cl_6$, $C_2Cl_5F$ and $C_2Cl_4F_2$ | 50.0 parts |
| $C_2Cl_3F_3$ | 78.9 parts |
| $C_2Cl_2F_4$ | 24.0 parts |
| Reactor 3: | |
| Temperature | 390° C. |
| Pressure | 1.5 absolute atmosphere |
| Contact time | 7.0 seconds |

This reactor is fed with dichlorotetrafluoroethane produced in the two first reactors, with 2.5 parts of hydrofluoric acid added.

The following is obtained at the exit of this reactor:

| $C_2Cl_3F_3$ | 2.9 parts |
| $C_2Cl_2F_4$ | 17.3 parts |
| $C_2ClF_5$ | 3.8 parts |

The dichlorotetrafluoroethane and chloropentafluoroethane are extracted from the operation. The undesired excess trichlorotrifluoroethane is recycled to reactor 1 with $C_2Cl_6$, $C_2Cl_5F$ and $C_2Cl_4F_2$.

EXAMPLE 4

The same catalyst is used as in Example 3. In order to assure the production of:

| | |
|---|---|
| $C_2Cl_2F_4$ | 6.5% |
| $C_2ClF_5$ | 93.5% | the following operating conditions are used:

| Reactor 1: | |
|---|---|
| Temperature | 420° C. |
| Pressure | 2.6 absolute atmospheres |
| Contact time | 6.0 seconds |

The feed to reactor 1 comprises the following:

| | |
|---|---|
| $Cl_2$ | 101.8 parts |
| HF | 488.5 parts |
| Recycled $C_2Cl_4$ | 50.5 parts |
| Recycled $C_2Cl_6$, $C_2Cl_5F$ and $C_2Cl_4F_2$ | 44.4 parts |
| Recycled $C_2Cl_3F_3$ | 108.2 parts |

The transformation rate of hydrofluoric acid is 65% in this reactor.

| Reactor 2: | |
|---|---|
| Temperature | 320° C. |
| Pressure | 2.1 absolute atmospheres |
| Contact time | 6.0 seconds |

The feed to reactor 2 comprises the effluents from reactor 1, with 100 parts of fresh tetrachloroethylene added.

At the exit, the total transformation rate of hydrofluoric acid is 85%. The organic effluents are composed of:

| | |
|---|---|
| $C_2Cl_4$ | 50.5 parts |
| $C_2Cl_6$, $C_2Cl_5F$, $C_2Cl_4F_2$ | 44.4 parts |
| $C_2Cl_3F_3$ | 93.8 parts |
| $C_2Cl_2F_4$ | 114.4 parts |
| Reactor 3: | |
| Temperature | 420° C. |
| Pressure | 1.5 absolute atmosphere |
| Contact time | 10.2 seconds |

Reactor 3 is fed with 114.4 parts of $C_2Cl_2F_4$ from reactor 2 and 245.8 parts of recycled $C_2Cl_2F_4$, to which 150.6 parts of hydrofluoric acid have been added.

At the exit of the reactor, the organic effluents contain:

| | |
|---|---|
| $C_2Cl_3F_3$ | 14.4 parts |
| $C_2Cl_2F_4$ | 252.1 parts |
| $C_2ClF_5$ | 90.0 parts |
| $C_2F_6$ | 3.6 parts |

All of the $C_2ClF_5$ and 6.3 parts of $C_2Cl_2F_4$ are taken out of the operation. The rest of $C_2Cl_2F_4$ is recycled to reactor 3, while all the $C_2Cl_3F_3$ produced is recycled to reactor 1.

EXAMPLE 5

In three fluidized bed reactors, a catalyst of chromium sulfate deposited on active carbon is used as described in French Patent Application No. 80.27660.

The following distribution of products of the reaction is desired:

| | |
|---|---|
| $C_2Cl_3F_3$ | 13.2% |
| $C_2Cl_2F_4$ | 80.1% |
| $C_2ClF_5$ | 6.7% |

Thus, the operating conditions are as follows:

| Reactor 1: | |
|---|---|
| Temperature | 400° C. |
| Pressure | 2.1 absolute atmospheres |
| Contact time | 6.0 seconds |
| Feeding to reactor 1: | |
| $Cl_2$ | 100.0 parts |
| HF | 489.3 parts |
| Recycled $C_2Cl_4$ | 47.0 parts |
| Recycled $C_2Cl_6$, $C_2Cl_5$ and $C_2Cl_4F_2$ | 35.0 parts |
| Recycled $C_2Cl_3F_3$ | 115.9 parts |

The transformation rate of hydrofluoric acid in this reactor is 54%.

| Reactor 2: | |
|---|---|
| Temperature | 300° C. |
| Pressure | 1.6 absolute atmosphere |
| Contact time | 4.0 seconds |

The reactor is fed with the effluents from reactor 1, with 100 parts of fresh tetrachloroethylene added.

The total transformation rate of hydrofluoric acid reaches 79% at the exit of this reactor and the composition of the organic effluents is as follows:

| | |
|---|---|
| $C_2Cl_4$ | 47.0 parts |
| $C_2Cl_6$, $C_2Cl_5F$ and $C_2Cl_4F_2$ | 35.0 parts |
| $C_2Cl_3F_3$ | 127.4 parts |
| $C_2Cl_2F_4$ | 88.5 parts |
| Reactor 3: | |
| Temperature | 385° C. |
| Pressure | 1.5 absolute atmosphere |
| Contact time | 9 seconds |

All the dichlorotetrafluoroethane issuing from reactor 2 is fed to reactor 3 at the same time as 12.8 parts of HF.

The effluents are made up of:

| | |
|---|---|
| $C_2Cl_3F_3$ | 1.7 parts |
| $C_2Cl_2F_4$ | 80.1 parts |
| $C_2ClF_5$ | 6.7 parts |

All of the dichlorotetrafluoroethane and chloropentafluoroethane are extracted from the operation, as well as 13.2 parts of trichlorotrifluoroethane. The rest of this product is recycled to reactor 1.

EXAMPLE 6

This is the same as in Example 5, but with the following operating conditions:

| Reactor 1: | |
|---|---|
| Temperature | 375° C. |
| Pressure | 2.5 absolute atmospheres |
| Contact time | 3.6 seconds |
| Feeding to Reactor 1: | |
| $Cl_2$ | 100 parts |
| HF | 444 parts |
| Recycled $C_2Cl_4$ | 71 parts |
| Recycled $C_2Cl_6$, $C_2Cl_5F$ and $C_2Cl_4F_2$ | 42 parts |
| Recycled $C_2Cl_3F_3$ | 129 parts |

The transformation rate of HF in this reaction is 74.5%.

| Reactor 2: | |
|---|---|
| Temperature | 290° C. |
| Pressure | 2.0 absolute atmospheres |
| Contact time | 4.1 seconds |

The reactor is fed with effluents from reactor 1, with 100 parts of fresh $C_2Cl_4$. The total transformation rate of HF in the first two reactors is 87.6%.

The composition of the organic effluents is as follows:

| $C_2Cl_4$ | 71 parts |
|---|---|
| $C_2Cl_6$, $C_2Cl_5F$ and $C_2Cl_4F_2$ | 42 parts |
| $C_2Cl_3F_3$ | 140 parts |
| $C_2Cl_2F_4$ | 89 parts |
| Reactor 3: | |
| Temperature | 400° C. |
| Pressure | 1.4 absolute atmosphere |
| Contact time | 8.9 seconds |

This reactor is fed with 89 parts of $C_2Cl_2F_4$ and 42 parts of HF. At the exit, the effluents contain:

| $C_2Cl_3F_3$ | 5 parts |
|---|---|
| $C_2Cl_2F_4$ | 65 parts |
| $C_2Cl\ F_5$ | 19 parts |

All of the $C_2Cl_2F_4$ and all of the $C_2Cl\ F_5$ are extracted from the operation, as well as 16 parts of $C_2Cl_3F_3$. The rest of $C_2Cl_3F_3$ is recycled to reactor 1 with the other underfluorinated products.

EXAMPLE 7

Still using the catalyst in Example 5 in the three reactors, but under the following conditions:

| Reactor 1: | |
|---|---|
| Temperature | 410° C. |
| Pressure | 2.6 absolute atmospheres |
| Contact time | 2.8 seconds |

The reactor 1 is fed by a mixture of:

| $Cl_2$ | 100 parts |
|---|---|
| HF | 350 parts |
| Recycled $C_2Cl_4$ | 39 parts |
| Recycled $C_2Cl_6$, $C_2Cl_5F$ and $C_2Cl_4F_2$ | 91 parts |
| Recycled $C_2Cl_3F_3$ | 74 parts |

The transformation rate of hydrofluoric acid at the exit is 60.8%.

| Reactor 2: | |
|---|---|
| Temperature | 280° C. |
| Pressure | 2.0 absolute atmospheres |
| Contact time | 2.5 seconds |

The reactor is fed with the effluents from reactor 1, with 100 parts of fresh tetrachloroethylene added.

The total transformation rate of hydrofluoric acid in the first two reactors is 98.5%.

The composition of the organic effluents is as follows:

| $C_2Cl_4$ | 39 parts |
|---|---|
| $C_2Cl_6$, $C_2Cl_5F$, $C_2Cl_4F_2$ | 91 parts |
| $C_2Cl_3F_3$ | 146 parts |
| $C_2Cl_2F_4$ | 28 parts |
| Reactor 3: | |
| Temperature | 400° C. |
| Pressure | 1.3 absolute atmosphere |
| Contact time | 9.5 seconds |

This reactor is fed with a mixture of 28 parts $C_2Cl_2F_4$ and 8 parts hydrofluoric acid.

At the exit, the following is obtained:

| $C_2Cl_3F_3$ | 1 part |
|---|---|
| $C_2Cl_2F_4$ | 23 parts |
| $C_2Cl\ F_5$ | 4 parts |

All of the $C_2Cl_2F_4$, all of the $C_2Cl\ F_5$ and 73 parts of $C_2Cl_3F_3$ are extracted from the operation. The rest of the $C_2Cl_3F_3$ is recycled to the first reactor with the other less-fluorinated products.

EXAMPLE 8

The three fluidized bed reactors are filled with a catalyst of chromium salts deposited on aluminum phosphate, as described in the French Patent Application No. 80.27662. Only 70% of $C_2Cl_2F_4$ and 30% of $C_2Cl\ F_5$ are the desired products. The operating conditions are as follows:

| Reactor 1: | |
|---|---|
| Temperature | 411° C. |
| Pressure | 2.2 absolute atmospheres |
| Contact time | 4.6 seconds |

The feed to reactor 1 is a mixture of:

| $Cl_2$ | 100 parts |
|---|---|
| HF | 443 parts |
| Recycled $C_2Cl_4$ | 32 parts |
| Recycled $C_2Cl_6$, $C_2Cl_5F$ and $C_2Cl_4F_2$ | 43 parts |

| | |
|---|---|
| Recycled C$_2$Cl$_3$F$_3$ | 91 parts |

The transformation rate of hydrofluoric acid is 56.9%.

| Reactor 2: | |
|---|---|
| Temperature | 305° C. |
| Pressure | 1.9 absolute atmosphere |
| Contact time | 4.2 seconds |

The reactor is fed with the effluents from reactor 1 mixed with 100 parts of fresh tetrachloroethylene.
At the exit, the gases contain:

| | |
|---|---|
| C$_2$Cl$_4$ | 32 parts |
| C$_2$Cl$_6$, C$_2$Cl$_5$F, C$_2$Cl$_4$F$_2$ | 43 parts |
| C$_2$Cl$_3$F$_3$ | 84 parts |
| C$_2$Cl$_2$F$_4$ | 106 parts |

The total transformation rate of hydrofluoric acid is 92%.

| Reactor 3: | |
|---|---|
| Temperature | 410° C. |
| Pressure | 0.9 absolute atmosphere |
| Contact time | 5.6 seconds |

The reactor is fed with 106 parts of C$_2$Cl$_2$F$_4$ and 55 parts of hydrofluoric acid. At the exit, the following is obtained:

| | |
|---|---|
| C$_2$Cl$_3$F$_3$ | 7 parts |
| C$_2$Cl$_2$F$_4$ | 70 parts |
| C$_2$Cl F$_5$ | 29 parts |

All the C$_2$Cl$_3$F$_3$ produced is recycled, while all the C$_2$Cl$_2$F$_4$ and C$_2$Cl F$_5$ is removed from the operation.

EXAMPLE 9

This is the same as Example 8, using the same catalyst, but the following production is desired:

| | |
|---|---|
| C$_2$Cl$_3$F$_3$ | 47% |
| C$_2$Cl$_2$F$_4$ | 42% |
| C$_2$Cl F$_5$ | 11% |

The three reactors then function under the following conditions:

| Reactor 1: | |
|---|---|
| Temperature | 408° C. |
| Pressure | 1.8 absolute atmosphere |
| Contact time | 5.7 seconds |

The reactor is fed with a mixture of:

| | |
|---|---|
| Cl$_2$ | 100 parts |
| HF | 384 parts |
| Recycled C$_2$Cl$_4$ | 71 parts |
| Recycled C$_2$Cl$_6$, C$_2$Cl$_5$F and C$_2$Cl$_4$F$_2$ | 32 parts |
| Recycled C$_2$Cl$_3$F$_3$ | 79 parts |

The transformation rate of hydrofluoric acid is 78.9%.

| Reactor 2: | |
|---|---|
| Temperature | 290° C. |
| Pressure | 1.1 absolute atmosphere |
| Contact time | 5.9 seconds |

This reactor is fed with the effluents from reactor 1 with 100 parts of fresh tetrachloroethylene added.
The total transformation rate of hydrofluoric acid in the two reactors reaches 94%.
The existing gases are composed of:

| | |
|---|---|
| C$_2$Cl$_4$ | 71 parts |
| C$_2$Cl$_6$, C$_2$Cl$_5$F, C$_2$Cl$_4$F$_2$ | 32 parts |
| C$_2$Cl$_3$F$_3$ | 122 parts |
| C$_2$Cl$_2$F$_4$ | 57 parts |
| Reactor 3: | |
| Temperature | 410° C. |
| Pressure | 0.9 absolute atmosphere |
| Contact time | 5.9 seconds |

The reactor is fed with a mixture of 57 parts of C$_2$Cl$_2$F$_4$ and 18 parts of hydrofluoric acid.
The following products are obtained at the exit:

| | |
|---|---|
| C$_2$Cl$_3$F$_3$ | 4 parts |
| C$_2$Cl$_2$F$_4$ | 42 parts |
| C$_2$Cl F$_5$ | 11 parts |

All the C$_2$Cl$_2$F$_4$, all the C$_2$Cl F$_5$ and 47 parts of C$_2$Cl$_3$F$_3$ are extracted from the operation, the rest being recycled with the less-fluorinated products to the first reactor.

We claim:
1. A continuous catalytic gaseous-phase process for the preparation of trichlorotrifluoroethane, dichlorotetrafluoroethane and monochloropentafluoroethane, in predetermined proportions, from tetrachloroethylene, chlorine and hydrofluoric acid comprising the steps of:
(a) reacting a mixture of chlorine, hydrofluoric acid and recycled products comprising tetrachloroethylene, hexachloroethane, pentachlorofluoroethane, tetrachlorodifluoroethane and trichlorodifluoroethane to produce a molar ratio of chlorine to recycled tetrachloroethylene of between about 1.1 and 5.0, in the gaseous phase in a first chlorination-fluorination reaction zone:
(b) mixing the gases leaving the first chlorination-fluorination reaction zone with fresh tetrachloroethylene to produce a molar ratio of chlorine to fresh tetrachloroethylene of between about 0.95 and 1.05;
(c) further reacting the effluent gases from the first chlorination-fluorination reaction zone with fresh tetrachloroethylene in a second gaseous-phase chlorination-fluorination reaction zone maintained at a lower temperature;
(d) feeding the effluents from the second reaction zone into a separation unit where the desired amounts of trichlorotrifluoroethane and di- chlorotetrafluoroethane are extracted and from which excess dichlorotetrafluoroethane is sent to a fluorination-dismutation reaction zone;

(e) reacting in the fluorination-dismutation reaction zone a mixture of hydrofluoric acid and dichlorotetrafluoroethane that has been recycled from the separation unit, in a molar ratio of between about 0.1 and 1 to produce chloropentafluoroethane;

(f) sending the effluents from the fluorination-dismutation reaction zone into the separation unit;

(g) treating the gaseous products in the separation unti to recover the unused hydrofluoric acid and extract predetermined quantities of chloropentafluoroethane, dichlorotetrafluoroethane and trichlorotrifluoroethane;

(h) recycling the untransformed tetrachloroethylene, hexachloroethane, pentachlorofluoroethane, tetrachlorodifluoroethane and the excess trichlorotrifluoroethane to the first reaction zone; and (i) recycling the excess dichlorotetrafluoroethane to the fluorination-dismutation reaction zone.

2. Process according to claim 1, wherein the extracted trichlorotrifluoroethane comprises less than 2% asymmetric isomer.

3. Process according to claim 1, wherein the extracted dichlorotetrafluoroethane comprises less than 7% asymmetric isomer.

4. Process according to claim 1, wherein the functioning pressure is between about 0.1 and 20 bars.

5. Process according to claim 4, wherein the reaction temperature of the first reaction zone is between about 300° and 500° C., the temperature of the second reaction zone is between about 250° and 450° C., and the temperature of the third reaction zone is between about 250° and 500° C.

6. Process according to claim 5, wherein the three reaction zones are fluidized bed reactors.

7. Process according to claim 5, wherein the two chlorination-fluorination reaction zones are fluidized bed reactors and the fluorination-dismutation reaction zone is a fixed bed reactor.

8. Process according to one of claims 6 or 7, wherein the catalysts in the reactors comprise supported or nonsupported oxides or halides of chromium, aluminum, cobalt, iron, titanium, nickel, copper, palladium or zirconium; an active carbon base impregnated with chromium trioxide or chromium sulfate; catalysts having a microsphere base of chromium oxide, or a base of chromium salts or oxides and aluminum phosphate.

9. Process according to claim 8, wherein the same catalyst is used in the three reactors.

* * * * *